US007789893B2

(12) United States Patent
Drasler et al.

(10) Patent No.: US 7,789,893 B2
(45) Date of Patent: Sep. 7, 2010

(54) METHOD AND APPARATUS FOR PROMOTING HEMOSTASIS OF A BLOOD VESSEL PUNCTURE

(75) Inventors: William Drasler, Minnetonka, MN (US); Mark Jenson, Greenfield, MN (US); Jason P. Hill, Cottage Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 740 days.

(21) Appl. No.: 11/531,143

(22) Filed: Sep. 12, 2006

(65) Prior Publication Data

US 2008/0065150 A1 Mar. 13, 2008

(51) Int. Cl.
*A61D 1/00* (2006.01)
(52) U.S. Cl. .................................................... 606/213
(58) Field of Classification Search ............... 600/115, 600/116, 117; 604/96.01, 101.01, 246, 99.02, 604/101.03, 101.04, 101.05, 102.01–102.03, 604/164.01–164.03, 30, 35, 509, 97.01, 98.01, 604/99, 1, 103.05, 103.06, 103.07, 525, 916, 604/917, 919, 920, 921, 164.08–164.09, 604/164.11, 164.13; 606/191, 192, 194, 606/198, 213–215; 607/1, 2, 3, 50, 122
See application file for complete search history.

(56) References Cited

U.S. PATENT DOCUMENTS

| 1,598,284 | A | * | 8/1926 | Kinney ..................... 604/99.02 |
| 4,024,873 | A | * | 5/1977 | Antoshkiw et al. ...... 604/101.04 |
| 4,324,262 | A | * | 4/1982 | Hall ............................ 600/569 |
| 4,445,892 | A | * | 5/1984 | Hussein et al. .......... 604/101.05 |
| 4,820,270 | A | * | 4/1989 | Hardcastle et al. ....... 604/96.01 |
| 5,074,845 | A | * | 12/1991 | Miraki et al. .......... 604/103.08 |
| 5,108,421 | A | | 4/1992 | Fowler |
| 5,192,300 | A | | 3/1993 | Fowler |
| 5,222,974 | A | | 6/1993 | Kensey et al. |
| 5,275,616 | A | | 1/1994 | Fowler |
| 5,282,827 | A | | 2/1994 | Kensey et al. |
| 5,300,023 | A | * | 4/1994 | Lowery et al. .............. 604/515 |
| 5,310,407 | A | | 5/1994 | Casale |
| 5,383,896 | A | | 1/1995 | Gershony et al. |

(Continued)

FOREIGN PATENT DOCUMENTS

WO   WO 2005/074364 A   8/2005

OTHER PUBLICATIONS

International Search Report PCT/US2007/075698; report dated Dec. 17, 2007.

(Continued)

*Primary Examiner*—Todd E Manahan
*Assistant Examiner*—Eric Blatt
(74) *Attorney, Agent, or Firm*—Crompton, Seager & Tufte LLC (57) ABSTRACT

An apparatus for promoting hemostasis of a puncture formed in a blood vessel accessible through an incision tract and methods of use thereof. The apparatus includes distal and proximal balloons each having a contracted position and an expanded position, the proximal balloon spaced by a predetermined initial distance from the distal balloon. The apparatus further includes at least one catheter coupling the distal and proximal balloons to a source of pressurized fluid to selectively actuate the distal and proximal balloons between the contracted and expanded positions.

8 Claims, 6 Drawing Sheets

U.S. PATENT DOCUMENTS

| | | | |
|---|---|---|---|
| 5,391,183 A | | 2/1995 | Janzen et al. |
| 5,441,517 A | | 8/1995 | Kensey et al. |
| 5,462,529 A | * | 10/1995 | Simpson et al. ........ 604/101.04 |
| 5,478,352 A | | 12/1995 | Fowler |
| 5,591,204 A | | 1/1997 | Janzen et al. |
| 5,591,205 A | | 1/1997 | Fowler |
| 5,601,602 A | | 2/1997 | Fowler |
| 5,626,601 A | | 5/1997 | Gershony et al. |
| 5,665,063 A | * | 9/1997 | Roth et al. ................... 604/509 |
| 5,676,689 A | | 10/1997 | Kensey et al. |
| 5,707,393 A | | 1/1998 | Kensey et al. |
| 5,725,498 A | | 3/1998 | Janzen et al. |
| 5,728,134 A | | 3/1998 | Barak |
| 5,741,223 A | | 4/1998 | Janzen et al. |
| 5,830,130 A | | 11/1998 | Janzen et al. |
| 5,861,004 A | | 1/1999 | Kensey et al. |
| 5,868,778 A | | 2/1999 | Gershony et al. |
| 5,948,425 A | | 9/1999 | Janzen et al. |
| 5,951,583 A | | 9/1999 | Jensen et al. |
| 5,957,952 A | | 9/1999 | Gershony et al. |
| 5,964,782 A | | 10/1999 | LaFontaine et al. |
| 6,007,563 A | | 12/1999 | Nash et al. |
| 6,017,359 A | | 1/2000 | Gershony et al. |
| 6,033,401 A | | 3/2000 | Edwards et al. |
| 6,048,358 A | | 4/2000 | Barak |
| 6,056,768 A | | 5/2000 | Cates et al. |
| 6,090,130 A | | 7/2000 | Nash et al. |
| 6,162,240 A | | 12/2000 | Cates et al. |
| 6,217,518 B1 | | 4/2001 | Holdaway et al. |
| 6,218,272 B1 | | 4/2001 | Yeom et al. |
| 6,246,898 B1 | | 6/2001 | Vesely et al. |
| 6,267,747 B1 | * | 7/2001 | Samson et al. ......... 604/103.07 |
| 6,296,658 B1 | | 10/2001 | Gershony et al. |
| 6,325,789 B1 | | 12/2001 | Janzen et al. |
| 6,371,975 B2 | | 4/2002 | Cruise et al. |
| 6,387,051 B1 | | 5/2002 | Ragauskas et al. |
| 6,458,147 B1 | | 10/2002 | Cruise et al. |
| 6,475,182 B1 | | 11/2002 | Hnojewyj et al. |
| 6,485,432 B1 | | 11/2002 | Stasz et al. |
| 6,504,289 B2 | | 1/2003 | Toda et al. |
| 6,562,059 B2 | | 5/2003 | Edwards et al. |
| 6,605,294 B2 | | 8/2003 | Sawhney |
| 6,656,136 B1 | | 12/2003 | Weng et al. |
| 6,699,261 B1 | | 3/2004 | Cates et al. |
| 6,703,047 B2 | | 3/2004 | Sawhney et al. |
| 6,733,515 B1 | | 5/2004 | Edwards et al. |
| 6,743,195 B2 | * | 6/2004 | Zucker .................. 604/101.01 |
| 6,743,248 B2 | | 6/2004 | Edwards et al. |
| 6,818,008 B1 | | 11/2004 | Cates et al. |
| 6,830,756 B2 | | 12/2004 | Hnojewyj |
| 6,835,178 B1 | | 12/2004 | Wilson et al. |
| 6,846,321 B2 | | 1/2005 | Zucker |
| 6,849,232 B2 | | 2/2005 | Ashby et al. |
| 7,008,441 B2 | | 3/2006 | Zucker |
| 7,081,125 B2 | | 7/2006 | Edwards et al. |
| 7,115,127 B2 | | 10/2006 | Lindenbaum et al. |
| 7,175,646 B2 | | 2/2007 | Brenneman et al. |
| 2003/0100921 A1 | | 5/2003 | Addis et al. |
| 2003/0191496 A1 | | 10/2003 | Edwards et al. |
| 2004/0009205 A1 | | 1/2004 | Sawhney |
| 2004/0098016 A1 | * | 5/2004 | Bonutti ...................... 606/192 |
| 2004/0106880 A1 | | 6/2004 | Weng et al. |
| 2004/0153060 A1 | | 8/2004 | Lindenbaum et al. |
| 2004/0172060 A1 | | 9/2004 | Cates et al. |
| 2004/0191277 A1 | | 9/2004 | Sawhney et al. |
| 2004/0249342 A1 | | 12/2004 | Khosravi et al. |
| 2004/0267193 A1 | | 12/2004 | Bagaoisan et al. |
| 2004/0267197 A1 | * | 12/2004 | Blankenship .......... 604/103.06 |
| 2004/0267307 A1 | | 12/2004 | Bagaoisan et al. |
| 2004/0267308 A1 | | 12/2004 | Bagaoisan et al. |
| 2005/0065549 A1 | | 3/2005 | Cates et al. |
| 2005/0080334 A1 | | 4/2005 | Willis |
| 2005/0149117 A1 | | 7/2005 | Khosravi et al. |
| 2005/0245876 A1 | | 11/2005 | Khosravi et al. |
| 2006/0034930 A1 | | 2/2006 | Khosravi et al. |
| 2006/0047313 A1 | | 3/2006 | Khanna et al. |
| 2006/0099238 A1 | | 5/2006 | Khosravi et al. |
| 2006/0100664 A1 | | 5/2006 | Pai et al. |
| 2006/0235376 A1 | | 10/2006 | Lindembaum et al. |
| 2006/0253072 A1 | | 11/2006 | Pai et al. |

OTHER PUBLICATIONS

U.S. Appl. No. 07/634,478, filed Dec. 27, 1990, Janzen.
U.S. Appl. No. 08/303,088, filed Sep. 8, 1994, Gershony.
U.S. Appl. No. 08/549,430, filed Oct. 27, 1995, Gershony.
U.S. Appl. No. 60/036,299, filed Mar. 12, 1997, Edwards.
U.S. Appl. No. 08/701,630, filed Aug. 22, 1996, Janzen.
U.S. Appl. No. 08/963,033, filed Nov. 3, 1997, Edwards.
U.S. Appl. No. 09/085,727, filed May 27, 1998, Janzen.
U.S. Appl. No. 09/334,300, filed Jun. 16, 1999, Edwards.

* cited by examiner

METHOD AND APPARATUS FOR PROMOTING HEMOSTASIS OF A BLOOD VESSEL PUNCTURE

FIELD OF THE DISCLOSURE

The present invention generally relates to methods and apparatus for performing vascular procedures, and more particularly, to devices and methods for sealing vascular puncture sites.

BACKGROUND OF THE DISCLOSURE

Various surgical procedures are performed using percutaneous entry into a blood vessel. To facilitate cardiovascular procedures, a small gauge needle is introduced through the skin and into a target blood vessel, often the femoral artery The needle forms a puncture through the blood vessel wall at the distal end of an incision tract that extends through the overlying tissue. A guidewire is then introduced through the bore of the needle, and the needle is withdrawn over the guidewire For procedures requiring the use of a larger cannula, one or more dilators may be passed over the guidewire to expand the tissue opening to larger sizes. When the tissue opening is the appropriate size, an introducer sheath is advanced over the guidewire and the dilator may be removed. The sheath and guidewire are left in place to provide access during subsequent procedures.

The sheath facilitates passage of a variety of diagnostic and therapeutic instruments and devices into the vessel and its tributaries. Illustrative diagnostic procedures include angiography, intravascular ultrasonic imaging, and the like. Exemplary interventional procedures include angioplasty, atherectomy, stent and graph placement, embolization, and the like. After the selected procedure is completed, the catheters, guidewire, and introducer sheath are removed, and it is necessary to close the vascular puncture to provide hemostasis to allow healing.

Traditional methods of achieving hemostasis include the application of external pressure to the skin entry site by a nurse or physician to stem bleeding from the wound until clotting and tissue rebuilding have sealed the perforation. In some situations, this pressure must be maintained for half an hour to an hour or more, during which the patient is uncomfortably immobilized, often with sandbags and the like. With externally applied manual pressure, both patient comfort and practitioner efficiency are impaired. Additionally, a risk of hematoma exists since bleeding from the vessel may continue until sufficient clotting effects hemostasis. Also, external pressure devices such as femoral compression systems, may be unsuitable for patients with substantial amounts of subcutaneous adipose tissue since the skin surface may be a considerable distance from the vascular puncture site, by rendering skin compression inaccurate and thus less effective. Moreover, the application of excessive pressure can occlude the underlying artery, resulting in ischemia and/or thrombosis inside the vessel.

Even after hemostasis has apparently been achieved, the patient must remain immobile and under observation for hours to prevent dislodgement of the clot and to assure that bleeding from the puncture wound does not resume. Renewed bleeding through the tissue tract is not uncommon and can result in hematoma, pseudoaneurisms, and arteriovenous fistulas. Such complications may require blood transfusion, surgical intervention, or other corrective procedures. The risk of these complications increases with the use of larger sheath sizes, which are frequently necessary interventional procedures, and when the patient is anticoagulated with heparin or other drugs.

Various procedures have been used to promote hemostasis without relying on skin surface pressure. Some of these proposals use intraluminal plugs and are characterized by the placement of an object within the blood stream of the vessel to close the puncture. Other proposals include delivery of tissue adhesive to the perforation site. Still further proposed solutions would insert a cylindrical plug into the incision tract that would subsequently expand and seal the puncture site. All of these approaches require either introducing or leaving foreign objects in patient's body and/or inserting a tubular probe of large diameter into the tissue channel left by the catheter in order to seal the puncture.

SUMMARY OF THE DISCLOSURE

In view of the foregoing, an apparatus is provided for promoting hemostasis of a puncture formed in a blood vessel accessible through an incision tract. The apparatus comprises a distal balloon having a contracted position, in which a profile of the distal balloon is sized for insertion through the blood vessel puncture, an expanded position, in which the distal balloon profile prevents passage through the blood vessel puncture. The apparatus comprises a proximal balloon spaced by a predetermined initial distance from the distal balloon and having a contracted position, in which a profile of the proximal balloon is sized for insertion through the incision tract, and an expanded position, in which the proximal balloon profile blocks passage through the blood vessel puncture. The apparatus further comprises at least one catheter coupling the distal and proximal balloons to a source of pressurized fluid to selectively actuate the distal and proximal balloons between the contracted and expanded positions. Still further, the apparatus comprises at least one rigid positioner associated with the at least one catheter to facilitate movement of the distal and proximal balloons proximally through the incision tract The catheter has a flexible wall portion extending proximally of the distal and proximal balloons to facilitate everting of the distal and proximal balloons as the catheter is proximally withdrawn from the incision tract.

In a refinement, the positioner comprises a rigid wall formed in the at least one catheter.

In a refinement, the distal and proximal balloons comprise distal and proximal balloon segments coupled to a single catheter.

In a refinement, the positioner comprises a rigid filament coupled to the distal balloon segment.

In a refinement, a transition section extends between the distal and proximal balloon segments and comprises circumferential bands formed of a rigid material to limit expansion of the transition section.

In a refinement, the distal balloon segment has a first wall thickness and the proximal balloon segment has a second wall thickness different from the first wall thickness.

In a refinement, the distal balloon is coupled to a first catheter having an outer wall and the proximal balloon is coupled to a second catheter having inner and outer walls, wherein the first catheter outer wall passes through the second catheter inner wall.

In a refinement, the first catheter further comprises a rigid inner wall defining a central lumen.

In a refinement, the positioner comprises the first catheter rigid inner wall.

In a refinement, the positioner comprises a rigid filament coupled to the distal balloon segment.

In a refinement, a method of promoting hemostasis of a puncture in a blood vessel accessible through an introducer sheath inserted in an incision tract is disclosed. The disclosed method comprises positioning distal and proximal balloons in the incision tract by advancing the distal and proximal balloons through the introducer sheath until the distal balloon is disposed within the blood vessel and the proximal balloon is disposed outside of the blood vessel; inflating the distal and proximal balloons; pulling the distal and proximal balloons in a proximal direction until the distal balloon engages an inner wall of the blood vessel; everting the distal balloon until it is withdrawn from the blood vessel; holding the proximal balloon in place for a period of time sufficient to at least initiate formation of thrombus; everting the proximal balloon; and withdrawing the distal and proximal balloons from the incision tract.

In a refinement, the method further comprises withdrawing the introducer sheath after positioning the distal and proximal balloons.

In a refinement, the method further comprises coupling the distal balloon to a first catheter having an outer wall and coupling the proximal balloon to a second catheter having inner and outer wall, and the first catheter outer wall passing through the second catheter inner wall.

In a refinement, the first catheter outer wall is flexible so that the distal balloon is everted by applying a proximal force to a center of the distal balloon.

In a refinement, the second catheter outer wall is flexible so that the proximal balloon is everted by applying a proximal force to the second catheter inner wall.

In a refinement, the distal and proximal balloons comprise distal and proximal balloon segments coupled to a single catheter.

In a refinement, the distal balloon is at least partially deflated prior to everting.

In a refinement, the method further comprises insetting the distal and proximal balloons into a positioning sheath prior to positioning in the incision tract

BRIEF DESCRIPTION OF THE DRAWINGS

The foregoing aspects and many of the attendant advantages of this disclose will become more readily appreciated as the same becomes better understood by reference to the following detailed description, when taken in conjunction with the accompanying drawings, wherein.

DETAILED DESCRIPTION OF THE DISCLOSURE

Apparatus and methods are disclosed for promoting hemostasis that allows a thrombosis to form at the puncture site and facilitate removal of the apparatus without disrupting the thrombosis The apparatus may include two balloons or balloon segments that are spaced from one another, with a distal balloon intended for insertion into the blood vessel to locate the apparatus and a proximal balloon inflatable to engage an exterior of the blood vessel. Both the distal and proximal balloons include flexible portions that allow the balloons to evert or turn inside out. Specifically, one wall of each balloon (i.e., either an inner or outer wall) may be pulled in a proximal direction so that the balloon collapses and rolls or peels away from the puncture area and incision tract, thereby minimizing the shear forces applied during withdrawal. The rolling action of the balloons initially generates a small force in the distal direction pushes the thrombosis toward the blood vessel, thereby to hold it in place. Subsequent rolling withdrawal of the balloons generates minimal forces in the proximal direction to minimize potential disruption of the thrombosis.

Figure 1:
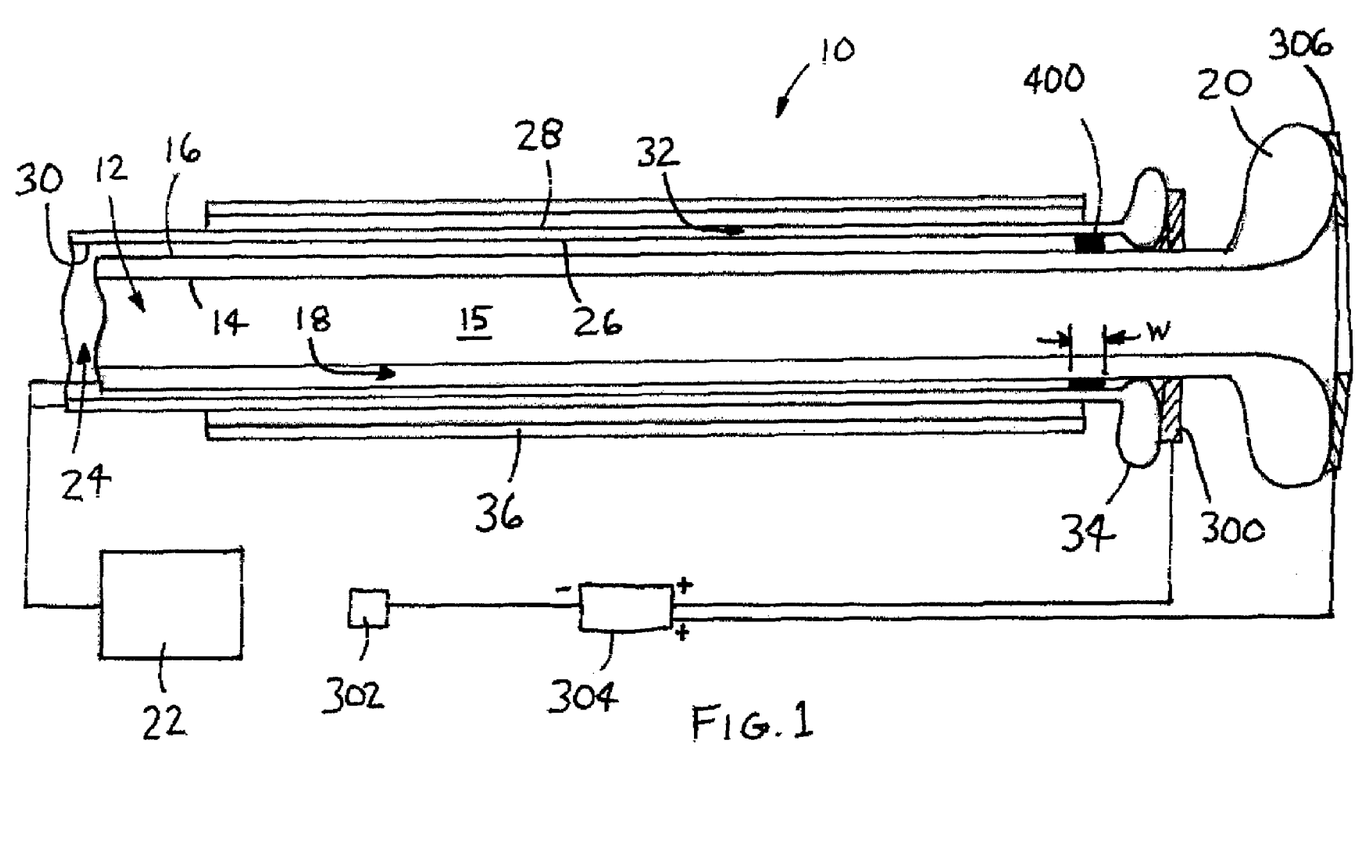
FIG. 1 is a side elevation view, in cross-section, of a dual balloon apparatus for promoting hemostasis of a blood vessel puncture, according to the present disclosure.

FIG. 1 illustrates an exemplary embodiment of apparatus 10 for closing a puncture in a blood vessel the apparatus 10 includes a first or inner catheter 12 having an inner wall 14 and an outer wall 16, with a fluid flow conduit 18 defined therebetween A first or distal balloon 20 is coupled to a distal end of the inner catheter 12, and an interior of the balloon 20 is in fluid communication with the conduit 18 The distal balloon 20 is formed of a flexible material that allows the balloon 20 to move between contracted and expanded positions. In the contracted position, a profile of the distal balloon 20 is reduced to allow insertion through an incision tract, as discussed in greater detail below. In the expanded position, as illustrated in FIG. 1, the distal balloon 20 is inflated with fluid to assume an enlarged profile A pressurized fluid source 22 fluidly communicates with a proximal end of the conduit 18. Fluid flow into an out of the conduit 18 is selectively controlled to actuate the distal balloon 20 between contracted and expanded positions.

In the illustrated embodiment, the inner catheter inner wall 14 defines a central lumen 15, which would allow the apparatus 10 to be passed over a guide wire (not shown) if desired. In the procedure described below, a plug (not shown) would be inserted into the central lumen 15 to prevent blood from passing through the central lumen 15.

The apparatus 10 also includes a second or outer catheter 24 also having an inner wall 26 and an outer wall 28. In the illustrated embodiment, the inner wall 26 of the catheter 24 defines a lumen 30 sized to receive the inner catheter 12. The inner and outer walls 26, 28 of the outer catheter 24 define a second fluid flow conduit 32 that is also in fluid communication with the source 22 of pressurized fluid. A second or proximal balloon 34 is coupled to a distal end of the outer catheter 24, and is formed of a flexible material which allows it be placed in contracted and expanded positions. An interior of the proximal balloon 34 is in fluid communication with the conduit 32 so that the proximal balloon 34 may be expanded or contracted by fluid flowing out of or in to the conduit 32, respectively. In the contracted position, the proximal balloon 34 has a reduced profile to facilitate insertion through an incision tact, as described in greater detail below. In the expanded position, the proximal balloon 34 is inflated to assume an enlarged profile, as illustrated in FIG. 1.

The inner and outer catheters 12, 24 are constructed to allow the associated distal and proximal balloons 20, 34 to be turned inside out, or everted, when withdrawn from an incision tract. To facilitate eversion, one or both of the inner and outer walls 14, 16 are formed of a pliant, flexible material. Suitable materials include elastomeric materials such as silicone, polyurethane, rubber, and related or similar materials Alternatively or additionally, other flexible polymers may be used, such as polyvinyl chloride, polymer blends, and composites of polymeric and filamentous materials, as long as the material or combination of materials as formed facilitate eversion of the catheters. In the exemplary embodiment illustrated in FIG. 1, the outer wall 16 is formed of the flexible material. Accordingly, a user may remove the catheter 12 simply by applying a proximal force to the proximal end of the inner wall 14 after the distal balloon 20 has been collapsed and returned to the contracted position The pulling force causes a distal-most portion of the catheter 12 to fold over on itself to form a distal tip. As additional catheter material is folded over, the distal tip recedes in the proximal direction in a rolling-type action Initially, slack in the balloon 20 causes the folded distal tip to move in the distal direction. Once the slack of the balloon 20 has been taken up, however, the remainder of the catheter 12 simply peels away from the outer catheter inner wall 26. When the catheter 12 is fully withdrawn from the incision tract in this manner, the distal balloon 20 is everted, or turned inside out The entire length of the outer wall 16 may be formed of flexible material. Alternatively, only a distal portion of the outer wall 16 is flexible. If only a distal portion is flexible, that portion should be sufficiently long to allow the catheter 12 to be lolled a safe distance away from the blood vessel puncture before resorting to sliding the catheter 12 out of the incision tract The outer catheter 24 is similarly adapted to evert the proximal balloon 34 during withdrawal. Accordingly, one or both of the inner and outer walls 26, 28 is formed of a flexible material. In the exemplary embodiment of FIG. 1, the outer wall 28 is formed of the flexible material. By applying a proximal force to the inner wall 26, the inner wall 26 is withdrawn from the incision tract as the catheter and balloon 34 fold over and are rolled out of the incision tract. The flexible outer wall 28 allows the catheter to fold over and peel away from the incision tract. As with the inner catheter 12, the entire length of the outer wall 28 of the outer catheter 24 may be formed of the flexible material. Alternatively, only a distal portion of the outer wall 28 is flexible so that the catheter 24 may be rolled away from the blood vessel puncture area before simply sliding the catheter 24 out of the incision tract.

The apparatus 10 may include a rigid positioner to assist in placing the apparatus 10 within the incision tract In the embodiment of FIG. 1, the positioner is provided by forming the inner walls 14, 26 of the catheters 12, 24 of a rigid material. Suitable rigid materials include polymeric materials such as polyethylene, PEBAX, polypropylene, polyester, and related of similar materials Alternatively or additionally, other rigid polymers may be used, such as fluoropolymers, polyimide, polyamide, surlyn, or higher-durometer formulations of polymers such as polyurethane or PVC, polymer blends, and composites of polymeric and filamentous materials. FIG. 1 also shows a rigid positioning sheath 36 which may be provided as an alternative or in addition to the rigid inner walls 14, 26 The exemplary positioning sheath 36 is illustrated as extending over at least a portion of the outer catheter 24, however it will be appreciated that the positioning sheath 36 may be disposed between the inner and outer catheters 12, 24 In addition, the apparatus 10 may include multiple positioning sheaths, such as a first positioning sheath around an exterior of the outer catheter 24 and a second positioning sheath disposed between the inner and outer catheter 12, 24. Regardless of the particular form in which the positioner is provided, it facilitates insertion of the apparatus 10 into the incision tract by supporting the flexible catheter material.

Figure 2A:
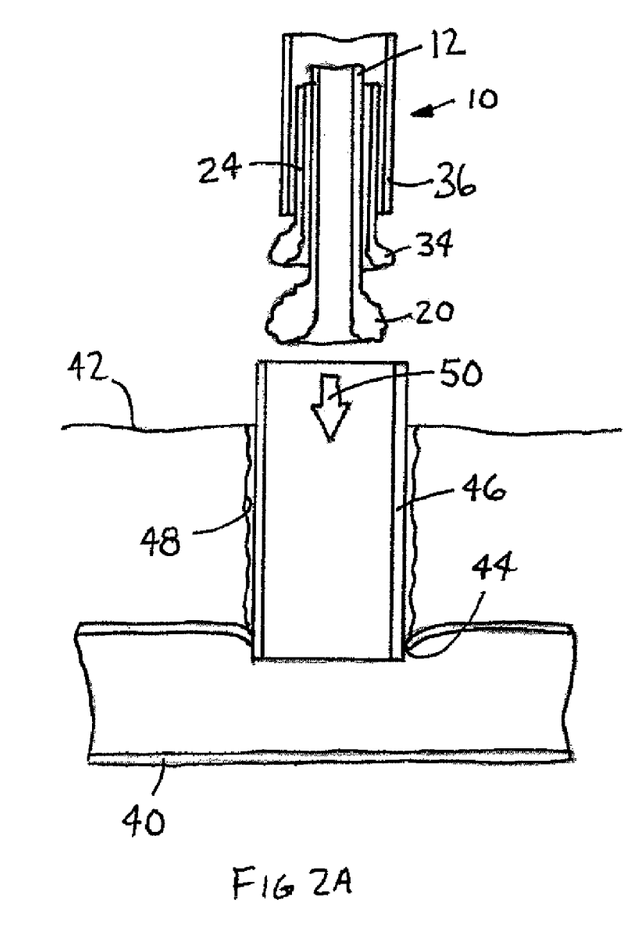
FIG. 2A is a side elevation view, in cross-section, of the hemostasis apparatus of FIG. 1 prior to insertion into an incision tract of a patient.

A method of promoting hemostasis of a blood pressure puncture is also disclosed, as illustrated in FIGS. 2A-E. As shown in FIG. 2A, a blood vessel 40 is located beneath the patient's skin surface 42, with a puncture 44 formed therein. The blood vessel puncture 44 is accessible via an incision tract 48 An introducer sheath 46 passes through the incision tract 48, and may be the same sheath 46 that was used during the previous intravascular procedure. As shown in FIG. 2A, any instruments used during the surgical procedure have been removed and the hemostasis apparatus 10 is positioned for insertion into the introducer sheath 46. The distal and proximal balloons 20, 34 are in their contracted positions to reduce their respective profiles, thereby facilitating insertion through the introducer sheath 46. With the hemostasis apparatus 10 aligned with the introducer sheath 46, the apparatus 10 is advanced in the distal direction, indicated by arrow 50, into the introducer sheath 46.

Figure 2B:
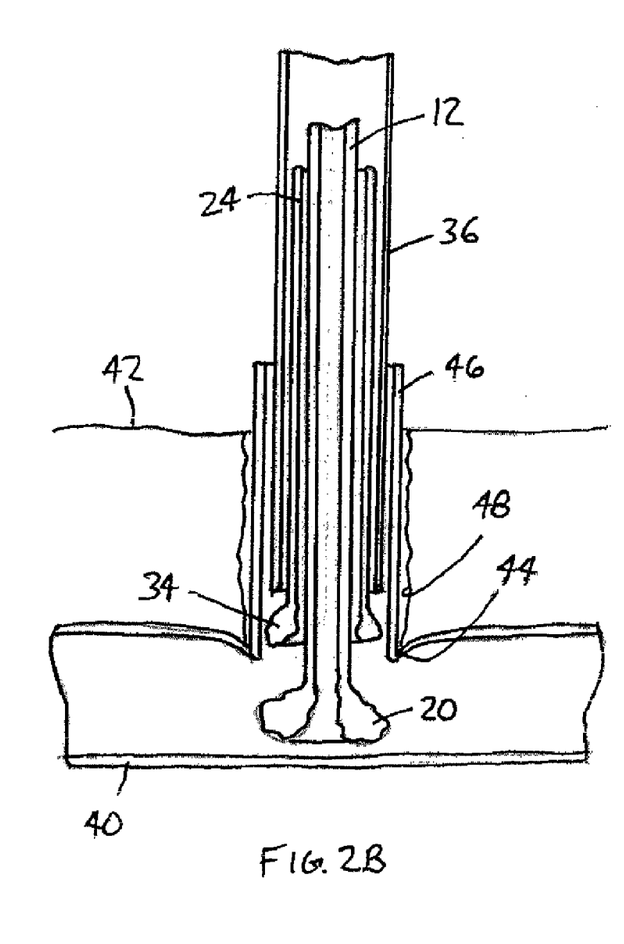
FIG. 2B is a side elevation view, in cross-section, of the hemostasis apparatus positioned within the patient's incision tract.
Figure 2C:
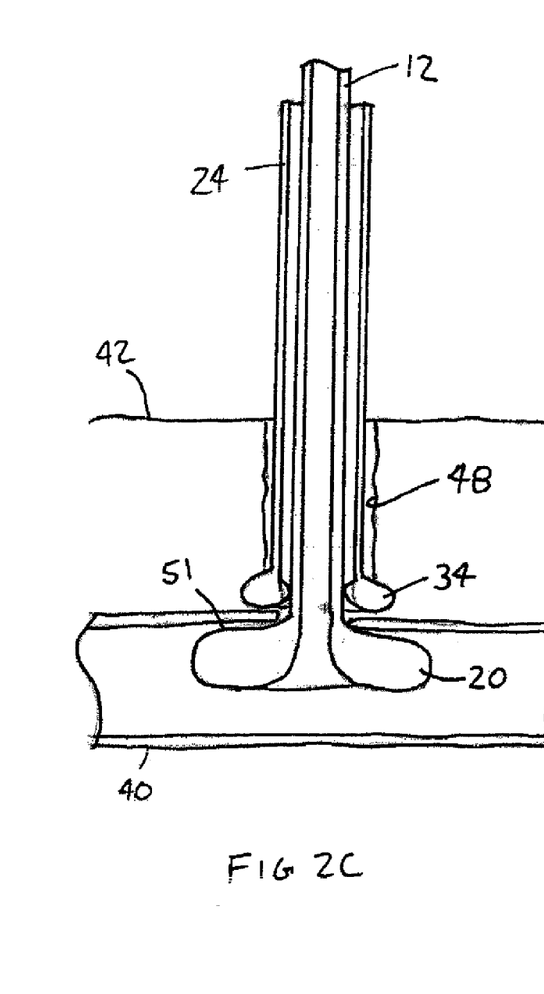
FIG. 2C is a side elevation view, in cross-section, of the hemostasis apparatus with both balloons inflated to an extended position.

The apparatus 10 is advanced distally until the distal balloon 20 is disposed inside the blood vessel 40 and the proximal balloon 34 is located outside of the blood vessel 40, as illustrated in FIG. 2B. With the balloons 20, 34 in this position, they may be inflated to their expanded positions as shown in FIG. 2C. In the expanded position, the distal balloon 20 has a profile which is larger than the puncture 44, and therefore it cannot be withdrawn proximally out of the blood vessel 40

As shown in FIG. 2C, the entire apparatus 10 may be moved proximally until a contact surface 51 of the distal balloon 20 engages an interior surface of the blood vessel 40. In this manner, the location of the blood vessel puncture 44 has been identified and the apparatus 10 is positioned accordingly.

Figure 2D:
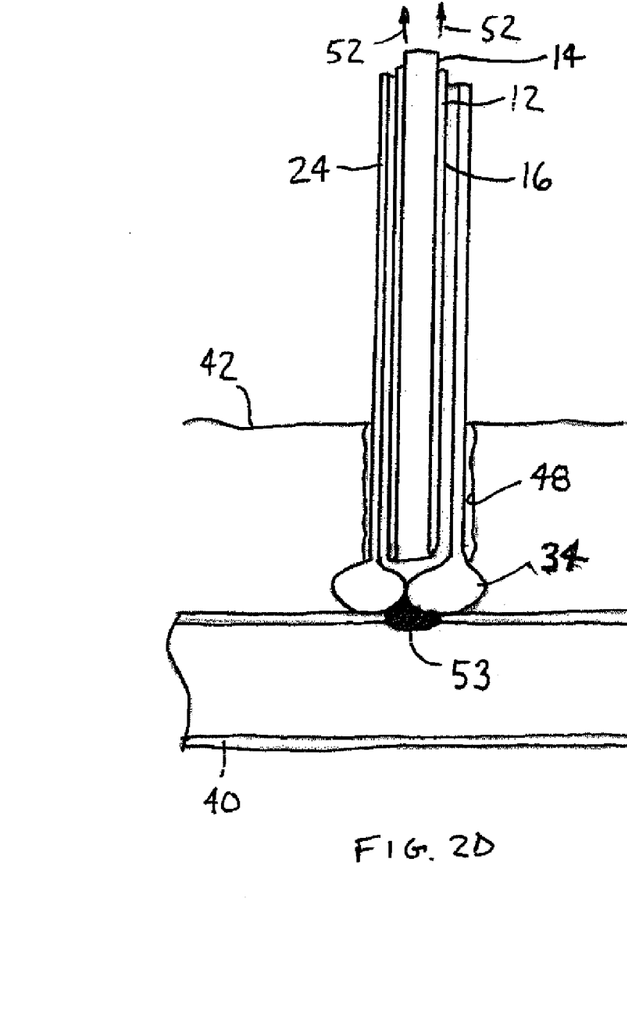
FIG. 2D is a side elevation view, in cross-section, of the hemostasis apparatus with a distal balloon withdrawn from the blood vessel.
Figure 2E:
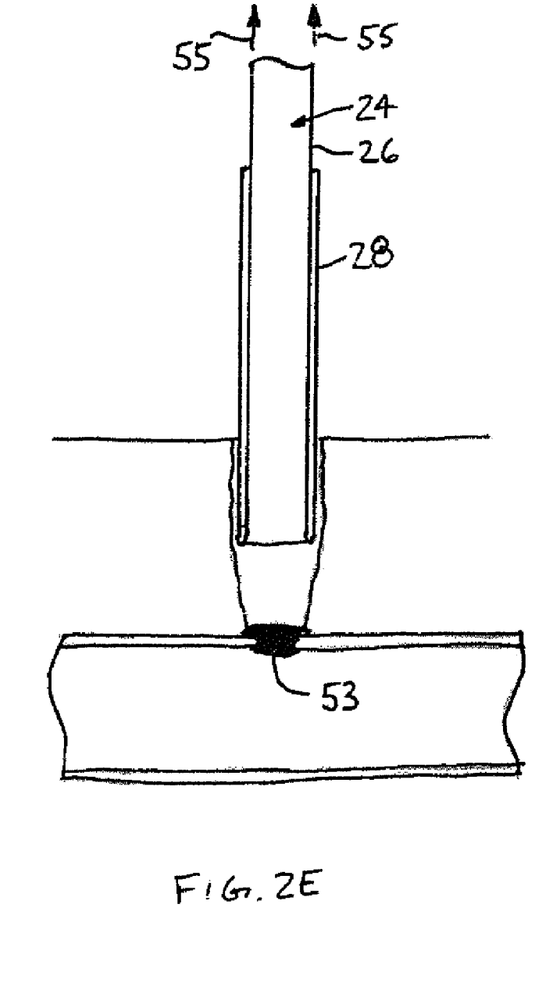
FIG. 2E is a side elevation view, in cross-section, of the hemostasis apparatus with the distal balloon fully withdrawn and the proximal balloon partially withdrawn from the incision tract.

After locating the blood vessel puncture 44, the distal balloon 20 may be deflated back to the contracted position. One of the catheter walls, such as inner wall 14, may be pulled in the proximal direction, indicated by arrows 52, so that the distal balloon 20 folds over and is rolled past a remainder of the catheter 12, as best shown in FIG. 2D. As the distal balloon 20 passes through the proximal balloon 34, the proximal balloon 34 expands to create a continuous barrier spanning across the blood vessel puncture 44. The proximal balloon 34 is held in this position for a period of time sufficient for thrombosis 53 to form The proximal balloon 34 is preferably positioned to engage in an exterior surface of the blood vessel 40 to minimize the risk of hematoma or other complications from blood leaking into the tissue surrounding the blood vessel 40

Figure 3:
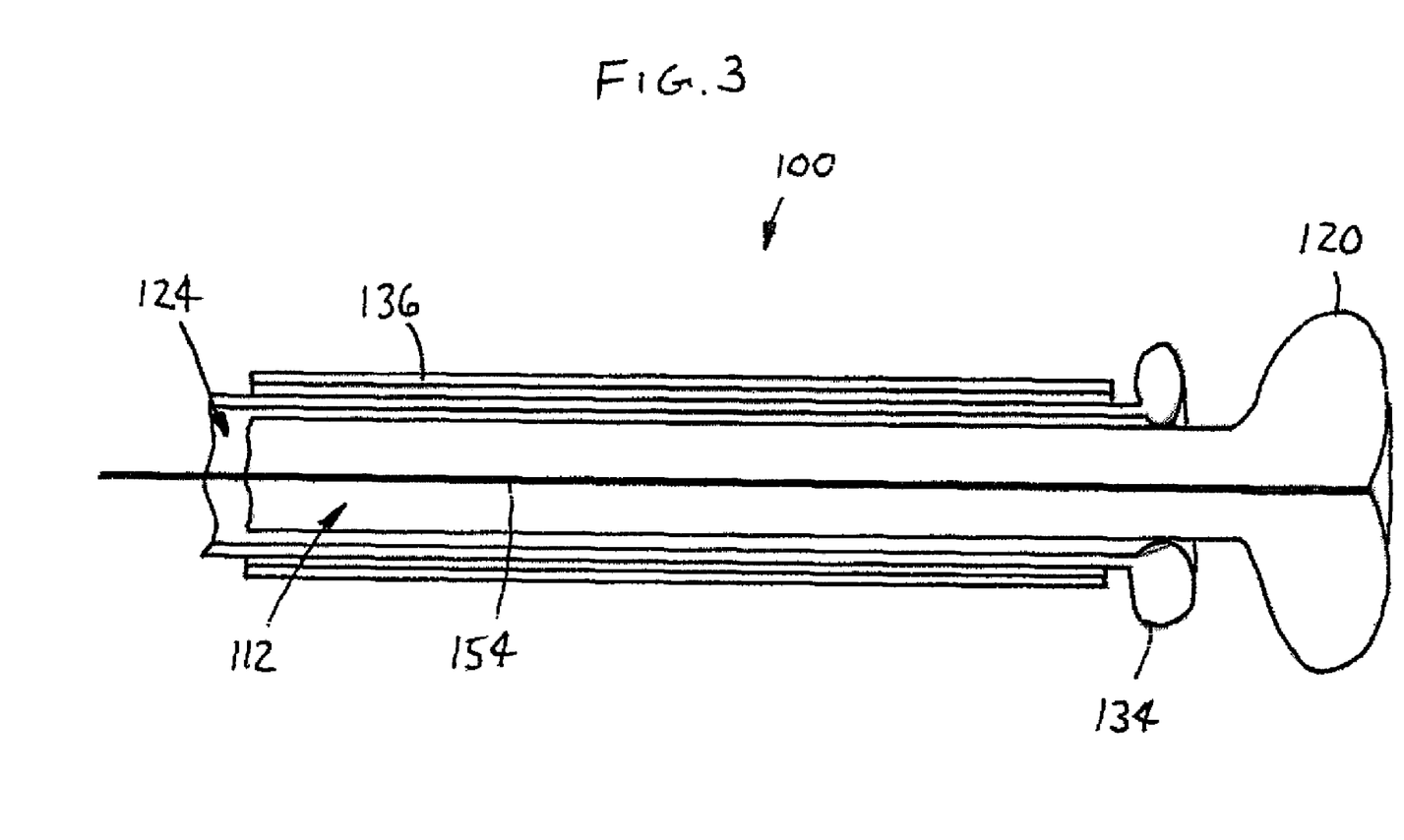
FIG. 3 is a side elevation view, in cross-section, of a second exemplary embodiment of a hemostasis apparatus according to the present disclosure.

Once thrombosis 53 has formed, the proximal balloon 34 and outer catheter 24 are removed. First, the balloon 34 is deflated to the contracted position. Next, the inner wall 26 is pulled in the proximal direction, indicated by arrows 55, so that the proximal balloon 34 and the outer catheter outer wall 28 are everted As noted above, the outer catheter 24 rolls over and therefore is peeled away from a surface of the incision tract 48, thereby minimizing forces that would tend to disturb the thrombosis 53 and surrounding tissue In an alternative embodiment illustrated in FIG. 3, a hemostasis apparatus 100 is provided having an inner catheter 112 without a central lumen. Instead, a positioner, such as a rigid filament 154, extends through a center of the inner catheter 12 and is coupled to a central portion of the distal balloon 120. An outer catheter 124 extends around the inner catheter 112 and includes a proximal balloon 134 A positioning sheath 136 is inserted over the outer catheter 124. Operation of the apparatus 100 is similar to that of the above embodiment, and therefore will not be described in detail, other than to note that the rigid filament 154 may be withdrawn proximally to evert the distal balloon 120

Figure 4:
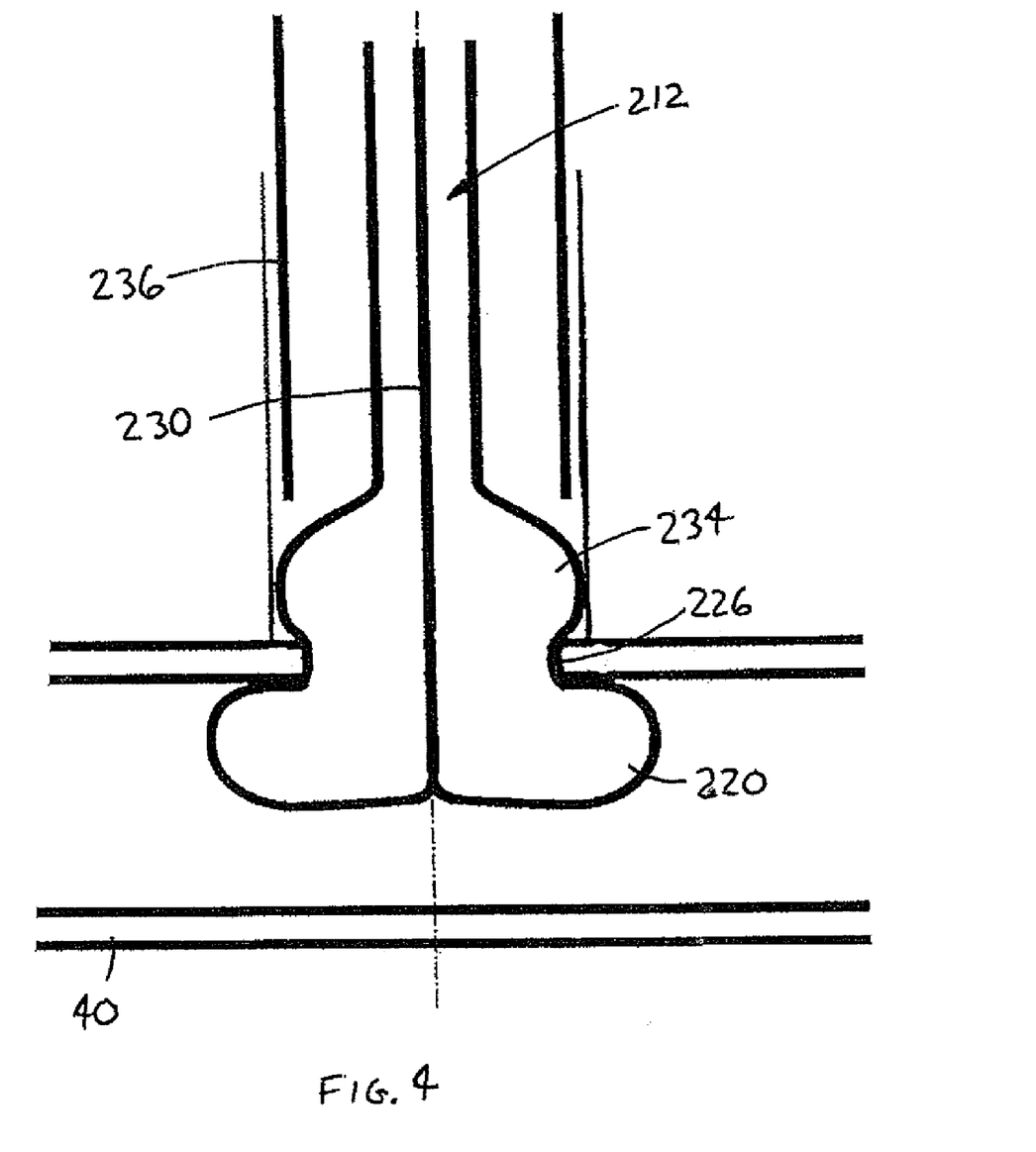
FIG. 4 is a side elevation view, in cross-section, of a third exemplary embodiment of a hemostasis apparatus according to the present disclosure

A third embodiment is illustrated in FIG. 4, wherein a single catheter 212 is coupled to distal and proximal balloon segments 220, 234. The balloon segments 220, 234 may be joined by a transition section 226 having a educed profile. The transition section 226 may be formed by the shape of the material forming the balloon segments or may be maintained by circumferential bands that limit expansion of the transition section 226 when the balloon segments 220, 234 are inflated. A rigid positioning sheath 236 is inserted over the catheter 212 to facilitate insertion of the catheter 212 into the incision tract. The distal and proximal balloon segments 220, 234 may have different material thicknesses that are responsive to different fluid pressures. As a result, a single source of pressurized fluid may be used to selectively expand and contract the distal and proximal balloon segments 220, 234 independent of each other. A rigid filament 230 extends through the catheter 212 and is coupled to a central portion of the distal balloon segment 220. Pulling the filament 230 in the proximal direction will withdraw the balloon segments 220, 234 from the incision tract and ultimately evert the balloon segments and catheter 212

To promote and expedite thrombosis formation at the blood vessel puncture, the hemostasis apparatus may include a source of positively charged electrical energy located near a distal end of the apparatus. A positive charge will attract negatively charged bodies, including platelets, found in the blood stream, and therefore such a charge positioned adjacent the blood vessel puncture will cause thrombosis to form more rapidly. For example, as schematically illustrated in FIG. 1, a first electrode 300 may be positioned on a distal end of the proximal balloon 34 while a second electrode 302 is positioned outside of the incision tract, such as on a patch applied to the skin surface of the patient. Additionally or alternatively, a third electrode 306 may be positioned on a surface of the distal balloon 20. An electrical source and associated controls 304 may be applied to the electrodes 300, 302, and 306 and oriented so that the first and/or third electrodes 300, 306 have positive charges while the second electrode 302 has a negative charge. In an exemplary embodiment, the first and third electrodes 300, 306 are formed from a metallized polymer that is incorporated into the associated balloon and/or catheter structure. While a particular arrangement of electrical components is disclosed above, it will be appreciated that various electrical polarities and waveforms may be used without departing from the scope of this disclosure. The electrodes are preferably incorporated into the balloon(s) as thin conductive layer(s), with a conductive path in a layer extending along the length of the inner catheter 12 and/or outer catheter 24 conducting the electrical energy from the electrical source 304 to the electrodes 300, 306 without interfering with the strength and flexibility properties of the catheters 12, 24 and balloons 20, 34, to allow eversion to occur as desired In embodiments employing two separate catheters, the catheters may be bonded together to simplify use during a vascular sealing procedure. As illustrated in FIG. 1, an optional bond 400 is provided between the catheters 12, 24. The bond is preferably located near the distal ends of the catheters 12, 24 to maintain a desired spacing between the balloons 20, 34, but spaced a sufficient distance proximally therefrom so as not to interfere with eversion of either balloon 20, 34. The bond 400 may also be positioned to allow the inner walls of balloon 34 to collapse and seal off the central lumen 15 as the balloon 20 is retracted. In the illustrated embodiment, the bond 400 has a width "W" that extends over a short distance of the overall longitudinal length of the catheters 12, 24. Additional bonds may be formed at between the catheters 12, 24 at points located proximally from the illustrated bond 400, or a continuous, wider bond may be formed between the catheters 12, 24 having a distal edge that is just proximal of the balloon 34.

During operation of the apparatus with the optional bond 400, the bonded catheters 12, 24 are introduced so that balloon 20 extends past introducer sheath 46 in the vessel. Balloon 20 is inflated, and the bonded catheters 12, 24 are withdrawn until balloon 20 contacts the end of introducer sheath 46. The bonded catheters 12, 24 and introducer sheath 46 may then be withdrawn until balloon 20 contacts the vessel wall. Balloon 20 and bonded catheters 12, 24 are then held in place while introducer sheath 46 is removed. In some embodiments, electrode 306 disposed on balloon 20 is activated when balloon 20 is in contact with the vessel wall Balloon 34 is then inflated. In some embodiments, electrode 300 is activated while balloon 34 is inflated. When used, positioning sheath 36 can be removed, preferably immediately before or immediately after inflation of balloon 34. Preferably while balloon 34 is inflated, balloon 20 is deflated and partially withdrawn by eversion until withdrawal is limited by the bonding of catheters 12 and 24. After passage of time to allow clotting to occur, and to allow electrical stimulation of clotting if used, balloon 34 is deflated. After determining whether sufficient hemostasis has been obtained, balloon 34 may be re-inflated in the same position, partially withdrawn (preferably, but not necessarily, by eversion) and re-inflated, or is removed by eversion together with catheter 12.

In any of the foregoing embodiments, supporting fibers may be incorporated into one or more walls of either catheter 12, 24. The supporting fibers may extend axially along the length of the catheters 12, 24 and may be formed of a material or otherwise configured to provide stiffness yet allow circumferential expansion of the catheters 12, 24 and balloons 20, 34. Alternatively or additionally, the supporting fibers may be oriented circumferentially to limit circumferential expansion of the associated catheter and/or balloon but still allow eversion. Still further, the supporting fibers may be disposed at other angles or orientations, and a particular catheter or balloon may incorporate multiple supporting fibers having different angles or orientations at different locations along that catheter or balloon.

While the foregoing was written with reference to specific examples and embodiments, it is to be understood that the scope of the invention is not to be limited thereby, but rather they are provided to satisfy best mode and enablement requirements while providing support for any and all claims which may issue herefrom.

What is claimed is:

1. A method of promoting hemostasis of a puncture in a blood vessel accessible through an introducer sheath inserted in an incision tract, the method comprising:

positioning distal and proximal balloons in the incision tract by advancing the distal and proximal balloons through the introducer sheath until the distal balloon is disposed within the blood vessel and the proximal balloon is disposed outside of the blood vessel;

inflating the distal and proximal balloons;

pulling the distal and proximal balloons in a proximal direction until the distal balloon engages an inner wall of the blood vessel;

everting the distal balloon until it is withdrawn from the blood vessel;

holding the proximal balloon in place for a period of time sufficient to at least initiate formation of thrombus;

everting the proximal balloon; and withdrawing the distal and proximal balloons from the incision tract.

2. The method of claim 1, in which the introducer sheath is withdrawn after positioning the distal and proximal balloons.

3. The method of claim 1, in which the distal balloon is coupled to a first catheter having an outer wall and the proximal balloon is coupled to a second catheter having inner and outer walls, wherein the first catheter outer wall passes through the second catheter inner wall.

4. The method of claim 3, in which the first catheter outer wall is flexible so that the distal balloon is everted by applying a proximal force to a center of the distal balloon.

5. The method of claim 3, in which the second catheter outer wall is flexible so that the proximal balloon is everted by applying a proximal force to the second catheter inner wall.

6. The method of claim 1, in which the distal and proximal balloons comprise distal and proximal balloon segments coupled to a single catheter.

7. The method of claim 1, in which the distal balloon is at least partially deflated prior to everting.

8. The method of claim 1, further comprising insetting the distal and proximal balloons into a positioning sheath prior to positioning in the incision tract.

* * * * *